United States Patent
Nanba et al.

(10) Patent No.: US 7,432,095 B2
(45) Date of Patent: Oct. 7, 2008

(54) FORMATE DEHYDROGENASE TOLERANT TO HALOGEN COMPOUNDS AND PROCESS FOR PRODUCING THE SAME

(75) Inventors: Hirokazu Nanba, Takasago (JP); Yasuko Takaoka, Kobe (JP)

(73) Assignee: Kaneka Corporation, Osaka (JP)

( * ) Notice: Subject to any disclaimer, the term of this patent is extended or adjusted under 35 U.S.C. 154(b) by 351 days.

(21) Appl. No.: 10/491,958

(22) PCT Filed: Oct. 9, 2002

(86) PCT No.: PCT/JP02/10460

§ 371 (c)(1),
(2), (4) Date: Jun. 23, 2004

(87) PCT Pub. No.: WO03/031626

PCT Pub. Date: Apr. 17, 2003

(65) Prior Publication Data

US 2005/0064569 A1    Mar. 24, 2005

(30) Foreign Application Priority Data

Oct. 9, 2001    (JP) ............................. 2001-312043

(51) Int. Cl.
- C12N 9/04 (2006.01)
- C12N 1/20 (2006.01)
- C12N 15/00 (2006.01)
- C12P 21/04 (2006.01)
- C07H 21/04 (2006.01)

(52) U.S. Cl. ............... 435/190; 435/69.1; 435/71.1; 435/252.3; 435/320.1; 435/252.33; 435/252.8; 435/252.34; 435/252.35; 435/252.32; 435/253.4; 435/440; 536/23.2; 536/23.7

(58) Field of Classification Search ............... 435/190, 435/69.1, 71.1, 252.3, 320.1, 252.33, 252.8, 435/440, 252.34, 252.35, 252.32, 253.4; 536/23.2, 23.7

See application file for complete search history.

(56) References Cited

U.S. PATENT DOCUMENTS 6,242,234 B1 *  6/2001  Kula et al. ................. 435/191

(Continued)

FOREIGN PATENT DOCUMENTS

EP    1 013 758 A2    6/2000

(Continued)

OTHER PUBLICATIONS

Popov et al. [NAD-dependent formate dehydrogenase from methylotrophic bacteria *Pseudomonas* sp. 101. 1. Amino acid sequence] Bioorg Khim. Mar. 1990;16(3):abstract.*

(Continued)

*Primary Examiner*—Yong D Pak
(74) *Attorney, Agent, or Firm*—Sughrue Mion, PLLC

(57) ABSTRACT

The invention provides a formate dehydrogenase having high specific activity, small Km values for formate and NAD, broad temperature and pH ranges of stability, broad temperature and pH ranges for action, and capable of regenerating a coenzyme with good efficiency in case of being present in an enzymatic reduction reaction system without inactivated.

The invention provides the enzyme mentioned above which has characteristics suited for industrial application by screening for soil formate dehydrogenase-producing microorganisms. The invention further provides a DNA containing the gene coding for the enzyme of the invention, a recombinant DNA constructed using a vector, and a transformant obtained by using this plasmid. The invention further provides a process for producing the formate dehydrogenase of the invention by using any microorganism of the genus *Thiobacillus* or a transformant constructed by using a formate dehydrogenase gene derived from above strain of microorganism, and a process for regenerating a coenzyme by using said enzyme in an enzymatic reduction system.

16 Claims, 4 Drawing Sheets

U.S. PATENT DOCUMENTS

| | | | |
|---|---|---|---|
| 6,258,565 B1 * | 7/2001 | Blatny et al. | 435/71.2 |
| 6,830,907 B2 * | 12/2004 | Mitsuhashi et al. | 435/190 |

FOREIGN PATENT DOCUMENTS

| | | |
|---|---|---|
| EP | 1211316 A1 | 6/2002 |
| JP | 60-241877 A | 11/1985 |
| JP | 60-241887 A | 11/1985 |
| JP | 63-313580 A | 12/1988 |
| JP | 3-61481 A | 3/1991 |
| JP | 10-23896 A | 1/1998 |
| JP | 2000-69971 A | 3/2000 |
| JP | 2000-78970 A | 3/2000 |
| JP | 2000-245471 A | 9/2000 |
| JP | 2002-223776 | 8/2002 |
| WO | WO 02/46427 A1 | 6/2002 |

OTHER PUBLICATIONS

Popov et al.—Sequence Alignment—SEQ ID No. 1.*

Branden et al. Introduction to Protein Structure, Garland Publishing Inc., New York, p. 247, 1991.*

Nanba et al. Biosci Biotechnol Biochem. Oct. 2003;67(10):2145-53.*

GIBCO BRL Products Catalog, Product Catalogue and Reference Guide, 16-1 through 16-15, 1995-1996.*

Galkin A et al., Cloning of formate dehydrogenase gene from a methanol-utilizing bacterium *Mycobacterium vaccae* N10., Appl Microbiol Biotechnol, Dec. 1995, 44 (3-4), pp. 479 to 483.

Chandra TS et al., Oxalate, formate, formamide, and methanol metabolism in *Thiobacillus novellas*., J. Bacteriol., Aug. 1977, 131 (2), pp. 389 t o398.

Wichmann, R., et al, "Continuous Enzymatic Transformation in an Enzyme Membrane Reactor with Simultaneous NAD(H) Regeneration", Biotechnology and Bioengineering, vol. 67, No. 6, Mar. 20, 2000, pp. 2791-2802 (XP-002356829).

Abalain, J. H., et al, "Cloning, DNA Sequencing and Expression of (3-17)Beta Hydroxysteroid Dehydrogenase from *Pseudomonas testosteroni*", The Journal of Steroid Biochemistry and Molecular Biology, vol. 44, No. 2, Feb. 1993, pp. 133-139 (XP-002356696).

Nanba, H., et al, "Purification and Characterization of an Alpha-Haloketone-Resistant Formate Dehydrogenase from *Thiobacillus* sp. Strain KNK65MA, and Cloning of the Gene", Bioscience, Biotechnology, and Biochemistry, vol. 67, No. 10, Oct. 2003, pp. 2145-2153 (XP-002356035).

Biochemical and Biophysical Research Communications, vol. 192, No. 2 pp. 976-981 (XP 001024075).

Database EMBL: "*Moraxella* sp. fdh gene", Database accession No. Y13245.

Neil A. Smith and Don P. Kelly: Mechanism of Oxidation of Dimethyl Disulphide by Thiobacillus Thioparus Strain E6; Journal of General Microbiology (1988), 134, 3031-3039.

J. T. Pronk, et al.: Engergetics of mixotropic and autotropic C1-metabolism by Thiobacillus acidophilus; Arch microbiol (1990) 154:576-583.

* cited by examiner

SEQUENCE LISTING

```
<160> NUMBER OF SEQ ID NOS: 11

<210> SEQ ID NO 1
<211> LENGTH: 401
<212> TYPE: PRT
<213> ORGANISM: Thiobacillus sp.

<400> SEQUENCE: 1

Met Ala Lys Ile Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

Gln Leu Leu Gly Ser Val Ser Gly Glu Leu Gly Leu Arg Lys Tyr Leu
    50                  55                  60

Glu Ala Asn Gly His Thr Phe Val Val Thr Ser Asp Lys Asp Gly Pro
65                  70                  75                  80

Asp Ser Val Phe Glu Lys Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Gly Ile Thr Val Ala Glu Val Thr
    130                 135                 140
```

```
Tyr Cys Asn Ser Ile Ser Val Ala Glu His Val Met Met Ile Leu
145                 150                 155                 160

Gly Leu Val Arg Asn Tyr Ile Pro Ser His Asp Trp Ala Arg Lys Gly
                165                 170                 175

Gly Trp Asn Ile Ala Asp Cys Val Glu His Ser Tyr Asp Leu Glu Gly
                180                 185                 190

Met Thr Val Gly Ser Val Ala Ala Gly Arg Ile Gly Leu Ala Val Leu
                195                 200                 205

Arg Arg Leu Ala Pro Phe Asp Val Lys Leu His Tyr Thr Asp Arg His
    210                 215                 220

Arg Leu Pro Glu Ala Val Glu Lys Glu Leu Gly Leu Val Trp His Asp
225                 230                 235                 240

Thr Arg Glu Asp Met Tyr Pro His Cys Asp Val Val Thr Leu Asn Val
                245                 250                 255

Pro Leu His Pro Glu Thr Glu His Met Ile Asn Asp Glu Thr Leu Lys
                260                 265                 270

Leu Phe Lys Arg Gly Ala Tyr Ile Val Asn Thr Ala Arg Gly Lys Leu
    275                 280                 285

Ala Asp Arg Asp Ala Ile Val Arg Ala Ile Glu Ser Gly Gln Leu Ala
290                 295                 300

Gly Tyr Ala Gly Asp Val Trp Phe Pro Gln Pro Ala Pro Lys Asp His
305                 310                 315                 320

Pro Trp Arg Thr Met Lys Trp Glu Gly Met Thr Pro His Ile Ser Gly
                325                 330                 335

Thr Ser Leu Ser Ala Gln Ala Arg Tyr Ala Ala Gly Thr Arg Glu Ile
                340                 345                 350

Leu Glu Cys Phe Phe Glu Gly Arg Pro Ile Arg Asp Glu Tyr Leu Ile
                355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Gly

<210> SEQ ID NO 2
<211> LENGTH: 1264
<212> TYPE: DNA
<213> ORGANISM: Thiobacillus sp.
<220> FEATURE:
<221> NAME/KEY: CDS
<222> LOCATION: (26)..(1228)

<400> SEQUENCE: 2
atacgcgcga gaggagatcc cggaa atg gcg aaa ata ctt tgc gtt ctc tat      52
                             Met Ala Lys Ile Leu Cys Val Leu Tyr
                              1               5 gat gat ccg gtc gac ggc tat ccg aag acc tat gcg cgc gac gat ctg     100
Asp Asp Pro Val Asp Gly Tyr Pro Lys Thr Tyr Ala Arg Asp Asp Leu
 10                  15                  20                  25 ccg aag atc gac cac tat ccg ggc ggg cag acc ctg ccg acg ccg aag     148
Pro Lys Ile Asp His Tyr Pro Gly Gly Gln Thr Leu Pro Thr Pro Lys
                 30                  35                  40 gcg atc gac ttc acc ccc ggc cag ctt ctc ggc tcg gtc tcc ggc gag     196
Ala Ile Asp Phe Thr Pro Gly Gln Leu Leu Gly Ser Val Ser Gly Glu
             45                  50                  55 ctg ggc ctg cgc aaa tat ctc gaa gcc aac ggc cac acc ttc gtc gtc     244
```

```
                Leu Gly Leu Arg Lys Tyr Leu Glu Ala Asn Gly His Thr Phe Val Val
                            60                  65                  70 acc tcc gac aag gac ggc ccg gat tcg gtg ttc gag aag gag ctc gtc           292
Thr Ser Asp Lys Asp Gly Pro Asp Ser Val Phe Glu Lys Glu Leu Val
    75                  80                  85 gac gcc gac gtg gtg atc tcc cag ccc ttc tgg ccg gcc tat ctg aca           340
Asp Ala Asp Val Val Ile Ser Gln Pro Phe Trp Pro Ala Tyr Leu Thr
90                  95                  100                 105 cct gag cgc atc gcc aag gcg aag aac ctg aag ctg gcg ctc acc gcc           388
Pro Glu Arg Ile Ala Lys Ala Lys Asn Leu Lys Leu Ala Leu Thr Ala
                110                 115                 120 ggc atc ggc tcc gat cac gtc gat ctt cag tcg gcg atc gac cgc ggc           436
Gly Ile Gly Ser Asp His Val Asp Leu Gln Ser Ala Ile Asp Arg Gly
            125                 130                 135 atc acc gtg gcc gaa gtc acc tac tgc aac tcg atc agc gtc gcc gag           484
Ile Thr Val Ala Glu Val Thr Tyr Cys Asn Ser Ile Ser Val Ala Glu
    140                 145                 150 cat gtg gtg atg atg atc ctc ggc ctg gtg cgc aac tac att ccc tcg           532
His Val Val Met Met Ile Leu Gly Leu Val Arg Asn Tyr Ile Pro Ser
155                 160                 165 cat gac tgg gcg cgc aag ggc ggc tgg aac ata gcc gac tgc gtg gag           580
His Asp Trp Ala Arg Lys Gly Gly Trp Asn Ile Ala Asp Cys Val Glu
170                 175                 180                 185 cac tcc tac gac ctc gag ggc atg acc gtc ggc tcc gtt gcc gcc ggc           628
His Ser Tyr Asp Leu Glu Gly Met Thr Val Gly Ser Val Ala Ala Gly
                190                 195                 200 cgc atc ggc ctc gcc gtg ctg cgc cgc ctc gcg ccc ttc gac gtg aag           676
Arg Ile Gly Leu Ala Val Leu Arg Arg Leu Ala Pro Phe Asp Val Lys
            205                 210                 215 ctg cac tac acc gac cgc cac cgc ctg ccg gaa gcg gtc gag aag gag           724
Leu His Tyr Thr Asp Arg His Arg Leu Pro Glu Ala Val Glu Lys Glu
    220                 225                 230 ttg ggc ctg gtc tgg cac gac acc cgc gag gac atg tac cca cat tgc           772
Leu Gly Leu Val Trp His Asp Thr Arg Glu Asp Met Tyr Pro His Cys
235                 240                 245 gac gtg gtc acg ctc aac gtg ccg ctg cat ccc gag acg gag cac atg           820
Asp Val Val Thr Leu Asn Val Pro Leu His Pro Glu Thr Glu His Met
250                 255                 260                 265 atc aat gac gag acg ctg aag ctg ttc aag cgc ggc gcc tat atc gtc           868
Ile Asn Asp Glu Thr Leu Lys Leu Phe Lys Arg Gly Ala Tyr Ile Val
                270                 275                 280 aac acc gcc cgc ggc aag ctc gcc gac cgc gac gcc atc gtg cgt gcg           916
Asn Thr Ala Arg Gly Lys Leu Ala Asp Arg Asp Ala Ile Val Arg Ala
            285                 290                 295 atc gag agc ggg cag ctc gcc ggc tat gct ggc gac gtg tgg ttc ccg           964
Ile Glu Ser Gly Gln Leu Ala Gly Tyr Ala Gly Asp Val Trp Phe Pro
    300                 305                 310 cag ccg gcg ccg aag gat cac ccc tgg cgc acc atg aag tgg gaa ggc          1012
Gln Pro Ala Pro Lys Asp His Pro Trp Arg Thr Met Lys Trp Glu Gly
315                 320                 325 atg acg ccg cac att tcc ggc acc tcg ctc tcc gcc cag gcg cgc tat          1060
Met Thr Pro His Ile Ser Gly Thr Ser Leu Ser Ala Gln Ala Arg Tyr
330                 335                 340                 345 gcg gcg ggc acg cgc gag atc ctc gaa tgc ttc ttc gaa ggt cgg ccg          1108
Ala Ala Gly Thr Arg Glu Ile Leu Glu Cys Phe Phe Glu Gly Arg Pro
                350                 355                 360 atc cgc gac gag tac ctg atc gtg cag ggc ggc gca ctc gcc ggc acg          1156
Ile Arg Asp Glu Tyr Leu Ile Val Gln Gly Gly Ala Leu Ala Gly Thr
            365                 370                 375
```

```
ggg gcg cat tcc tac tcc aag ggc aat gcg acc ggc ggc tcg gaa gag      1204
Gly Ala His Ser Tyr Ser Lys Gly Asn Ala Thr Gly Gly Ser Glu Glu
        380                 385                 390 gcc gcg aag ttc aag aag gcc ggc tgatccctcc cgagacacag accgaccagg     1258
Ala Ala Lys Phe Lys Lys Ala Gly
        395                 400 cgaacg                                                                1264

<210> SEQ ID NO 3
<211> LENGTH: 1206
<212> TYPE: DNA
<213> ORGANISM: Thiobacillus sp.
<220> FEATURE:
<221> NAME/KEY: CDS
<222> LOCATION: (1)..(1203)

<400> SEQUENCE: 3 atg gcg aaa ata ctt tgc gtt ctc tat gat gat ccg gtc gac ggc tat       48
Met Ala Lys Ile Leu Cys Val Leu Tyr Asp Asp Pro Val Asp Gly Tyr
1               5                   10                  15 ccg aag acc tat gcg cgc gac gat ctg ccg aag atc gac cac tat ccg       96
Pro Lys Thr Tyr Ala Arg Asp Asp Leu Pro Lys Ile Asp His Tyr Pro
                20                  25                  30 ggc ggg cag acc ctg ccg acg ccg aag gcg atc gac ttc acc ccc ggc      144
Gly Gly Gln Thr Leu Pro Thr Pro Lys Ala Ile Asp Phe Thr Pro Gly
            35                  40                  45 cag ctt ctc ggc tcg gtc tcc ggc gag ctg ggc ctg cgc aaa tat ctc      192
Gln Leu Leu Gly Ser Val Ser Gly Glu Leu Gly Leu Arg Lys Tyr Leu
        50                  55                  60 gaa gcc aac ggc cac acc ttc gtc gtc acc tcc gac aag gac ggc ccg      240
Glu Ala Asn Gly His Thr Phe Val Val Thr Ser Asp Lys Asp Gly Pro
65                  70                  75                  80 gat tcg gtg ttc gag aag gag ctc gtc gac gcc gac gtg gtg atc tcc      288
Asp Ser Val Phe Glu Lys Glu Leu Val Asp Ala Asp Val Val Ile Ser
                85                  90                  95 cag ccc ttc tgg ccg gcc tat ctg aca cct gag cgc atc gcc aag gcg      336
Gln Pro Phe Trp Pro Ala Tyr Leu Thr Pro Glu Arg Ile Ala Lys Ala
                100                 105                 110 aag aac ctg aag ctg gcg ctc acc gcc ggc atc ggc tcc gat cac gtc      384
Lys Asn Leu Lys Leu Ala Leu Thr Ala Gly Ile Gly Ser Asp His Val
            115                 120                 125 gat ctt cag tcg gcg atc gac cgc ggc atc acc gtg gcc gaa gtc acc      432
Asp Leu Gln Ser Ala Ile Asp Arg Gly Ile Thr Val Ala Glu Val Thr
        130                 135                 140 tac tgc aac tcg atc agc gtc gcc gag cat gtg gtg atg atg atc ctc      480
Tyr Cys Asn Ser Ile Ser Val Ala Glu His Val Val Met Met Ile Leu
145                 150                 155                 160 ggc ctg gtg cgc aac tac att ccc tcg cat gac tgg gcg cgc aag ggc      528
Gly Leu Val Arg Asn Tyr Ile Pro Ser His Asp Trp Ala Arg Lys Gly
                165                 170                 175 ggc tgg aac ata gcc gac tgc gtg gag cac tcc tac gac ctc gag ggc      576
Gly Trp Asn Ile Ala Asp Cys Val Glu His Ser Tyr Asp Leu Glu Gly
            180                 185                 190 atg acc gtc ggc tcc gtt gcc gcc ggc cgc atc ggc ctc gcc gtg ctg      624
Met Thr Val Gly Ser Val Ala Ala Gly Arg Ile Gly Leu Ala Val Leu
        195                 200                 205 cgc cgc ctc gcg ccc ttc gac gtg aag ctg cac tac acc gac cgc cac      672
Arg Arg Leu Ala Pro Phe Asp Val Lys Leu His Tyr Thr Asp Arg His
    210                 215                 220 cgc ctg ccg gaa gcg gtc gag aag gag ttg ggc ctg gtc tgg cac gac      720
Arg Leu Pro Glu Ala Val Glu Lys Glu Leu Gly Leu Val Trp His Asp
```

-continued

| | | | | | | | | | | | | | |
|---|---|---|---|---|---|---|---|---|---|---|---|---|---|
| | | 225 | | | 230 | | | 235 | | | 240 | | |
| acc | cgc | gag | gac | atg | tac | cca | cat | tgc | gac | gtg | gtc | acg | ctc | aac | gtg | 768 |
| Thr | Arg | Glu | Asp | Met | Tyr | Pro | His | Cys | Asp | Val | Val | Thr | Leu | Asn | Val |
| | | 245 | | | | | 250 | | | | | 255 | | |
| ccg | ctg | cat | ccc | gag | acg | gag | cac | atg | atc | aat | gac | gag | acg | ctg | aag | 816 |
| Pro | Leu | His | Pro | Glu | Thr | Glu | His | Met | Ile | Asn | Asp | Glu | Thr | Leu | Lys |
| | | | 260 | | | | | 265 | | | | | 270 | | |
| ctg | ttc | aag | cgc | ggc | gcc | tat | atc | gtc | aac | acc | gcc | cgc | ggc | aag | ctc | 864 |
| Leu | Phe | Lys | Arg | Gly | Ala | Tyr | Ile | Val | Asn | Thr | Ala | Arg | Gly | Lys | Leu |
| | | 275 | | | | | 280 | | | | | 285 | | | |
| gcc | gac | cgc | gac | gcc | atc | gtg | cgt | gcg | atc | gag | agc | ggg | cag | ctc | gcc | 912 |
| Ala | Asp | Arg | Asp | Ala | Ile | Val | Arg | Ala | Ile | Glu | Ser | Gly | Gln | Leu | Ala |
| 290 | | | | | 295 | | | | | 300 | | | | | |
| ggc | tat | gct | ggc | gac | gtg | tgg | ttc | ccg | cag | ccg | gcg | ccg | aag | gat | cac | 960 |
| Gly | Tyr | Ala | Gly | Asp | Val | Trp | Phe | Pro | Gln | Pro | Ala | Pro | Lys | Asp | His |
| 305 | | | | | 310 | | | | | 315 | | | | | 320 |
| ccc | tgg | cgc | acc | atg | aag | tgg | gaa | ggc | atg | acg | ccg | cac | att | tcc | ggc | 1008 |
| Pro | Trp | Arg | Thr | Met | Lys | Trp | Glu | Gly | Met | Thr | Pro | His | Ile | Ser | Gly |
| | | | 325 | | | | | 330 | | | | | 335 | | |
| acc | tcg | ctc | tcc | gcc | cag | gcg | cgc | tat | gcg | gcg | ggc | acg | cgc | gag | atc | 1056 |
| Thr | Ser | Leu | Ser | Ala | Gln | Ala | Arg | Tyr | Ala | Ala | Gly | Thr | Arg | Glu | Ile |
| | | 340 | | | | | 345 | | | | | 350 | | | |
| ctc | gaa | tgc | ttc | ttc | gaa | ggt | cgg | ccg | atc | cgc | gac | gag | tac | ctg | atc | 1104 |
| Leu | Glu | Cys | Phe | Phe | Glu | Gly | Arg | Pro | Ile | Arg | Asp | Glu | Tyr | Leu | Ile |
| | 355 | | | | | 360 | | | | | 365 | | | | |
| gtg | cag | ggc | ggc | gca | ctc | gcc | ggc | acg | ggg | gcg | cat | tcc | tac | tcc | aag | 1152 |
| Val | Gln | Gly | Gly | Ala | Leu | Ala | Gly | Thr | Gly | Ala | His | Ser | Tyr | Ser | Lys |
| 370 | | | | | 375 | | | | | 380 | | | | | |
| ggc | aat | gcg | acc | ggc | ggc | tcg | gaa | gag | gcc | gcg | aag | ttc | aag | aag | gcc | 1200 |
| Gly | Asn | Ala | Thr | Gly | Gly | Ser | Glu | Glu | Ala | Ala | Lys | Phe | Lys | Lys | Ala |
| 385 | | | | | 390 | | | | | 395 | | | | | 400 |
| ggc | tga | | | | | | | | | | | | | | | 1206 |
| Gly | | | | | | | | | | | | | | | | |

<210> SEQ ID NO 4
<211> LENGTH: 17
<212> TYPE: DNA
<213> ORGANISM: Artificial Sequence
<220> FEATURE:
<223> OTHER INFORMATION: primer 1
<220> FEATURE:
<221> NAME/KEY: misc_feature
<222> LOCATION: (3)..(3)
<223> OTHER INFORMATION: "n" may be any nucleotide
<220> FEATURE:
<221> NAME/KEY: misc_feature
<222> LOCATION: (9)..(9)
<223> OTHER INFORMATION: "n" may be any nucleotide
<220> FEATURE:
<221> NAME/KEY: misc_feature
<222> LOCATION: (12)..(12)
<223> OTHER INFORMATION: "n" may be any nucleotide

<400> SEQUENCE: 4
gcnaaratnc tntgygt                                                17

<210> SEQ ID NO 5
<211> LENGTH: 20
<212> TYPE: DNA
<213> ORGANISM: Artificial Sequence
<220> FEATURE:
<223> OTHER INFORMATION: primer 2
<220> FEATURE:
<221> NAME/KEY: misc_feature
<222> LOCATION: (6)..(6)

-continued

```
<223> OTHER INFORMATION: "n" may be any nucleotide
<220> FEATURE:
<221> NAME/KEY: misc_feature
<222> LOCATION: (15)..(15)
<223> OTHER INFORMATION: "n" may be any nucleotide

<400> SEQUENCE: 5
ggytgnggra accanacrtc                                              20

<210> SEQ ID NO 6
<211> LENGTH: 25
<212> TYPE: DNA
<213> ORGANISM: Artificial Sequence
<220> FEATURE:
<223> OTHER INFORMATION: primer 3

<400> SEQUENCE: 6
tagtggtcga tcttcggcag atcgt                                        25

<210> SEQ ID NO 7
<211> LENGTH: 20
<212> TYPE: DNA
<213> ORGANISM: Artificial Sequence
<220> FEATURE:
<223> OTHER INFORMATION: primer 4

<400> SEQUENCE: 7
gagacgctga agctgttcaa                                              20

<210> SEQ ID NO 8
<211> LENGTH: 27
<212> TYPE: DNA
<213> ORGANISM: Artificial Sequence
<220> FEATURE:
<223> OTHER INFORMATION: primer 5

<400> SEQUENCE: 8
acactgcaga tacgcgcgag aggagat                                      27

<210> SEQ ID NO 9
<211> LENGTH: 28
<212> TYPE: DNA
<213> ORGANISM: Artificial Sequence
<220> FEATURE:
<223> OTHER INFORMATION: primer 6

<400> SEQUENCE: 9
tctgaattcg ttcgcctggt cggtctgt                                     28

<210> SEQ ID NO 10
<211> LENGTH: 24
<212> TYPE: DNA
<213> ORGANISM: Artificial Sequence
<220> FEATURE:
<223> OTHER INFORMATION: primer 7

<400> SEQUENCE: 10
acgcatatgg cgaaaatact ttgc                                         24

<210> SEQ ID NO 11
<211> LENGTH: 30
<212> TYPE: DNA
<213> ORGANISM: Artificial Sequence
<220> FEATURE:
<223> OTHER INFORMATION: primer 8
```

```
<400> SEQUENCE: 11
agtctgcagt tatcagccgg ccttcttgaa                                          30
```

FORMATE DEHYDROGENASE TOLERANT TO HALOGEN COMPOUNDS AND PROCESS FOR PRODUCING THE SAME

TECHNICAL FIELD

The present invention relates to a polypeptide tolerant to haloketone compounds and having formate dehydrogenase activity, a gene coding for it, a process for producing a formate dehydrogenase with the aid of a strain of microorganism capable of producing said polypeptide or a transformant thereof, and a process for regenerating a coenzyme with good efficiency which comprises permitting said enzyme to be present in an enzymatic reduction reaction system.

BACKGROUND ART

The enzyme formate dehydrogenase (enzyme no. [EC1.2.1.2]) is an enzyme which catalyzes the reaction giving rise to carbon dioxide and reduced nicotine adenine dinucleotide (hereinafter referred to as NADH) from a formate and oxidized nicotine adenine dinucleotide (hereinafter referred to as NAD). Formate dehydrogenase is a useful enzyme having advantages that when it is used for coenzyme regeneration in a NADH-dependent enzymatic reaction, an inexpensive formate can be utilized and the byproduct is carbon dioxide which is not accumulated in the system. Furthermore, as an enzyme having small Km values for formate and NAD, this enzyme acts effectively at low substrate concentrations and can be utilized for specific microassay of formate, thus being an industrially useful enzyme.

Formate dehydrogenase is known to exist in higher plants, methanol-utilizing yeasts, bacteria, and the like. The enzyme which has heretofore been purified and characterized includes the enzyme derived from the higher plant pea (*Pisum sativum*: J. Biochem., vol. 77, 845, 1975) and the enzymes derived from methanol-utilizing yeast species, namely Candida boidinii (Eur. J. Biochem., vol. 62, 151, 1976), *Candida methylica* (Eur. J. Biochem. vol. 152, 657, 1985), *Candida methanolica* (FEMS Microbiol. Lett., vol. 48, 139, 1987), *Kloeckera* sp. (Agric. Biol. Chem., vol. 38, 111, 1974), *Pichia pastoris* (Agric. Biol. Chem., vol. 47, 2547, 1983), and *Lipomyces methanosilviensis* (JP-A-60-241887), among others. However, these enzymes invariably have some or other shortcomings to be overcome for industrial application, namely low specific activity, large Km values for formate and NAD, and/or a narrow pH range for activity.

There also are several enzymes which have been purified from bacteria and characterized but each has its own drawback in industrial application. For example, the enzymes derived from *Pseudomonas* sp. 101 (Eur. J. Biochem., vol. 99, 569, 1979) and *Pseudomonas oxalaticus* (Eur. J. Biochem., vol. 83, 485, 1978) have comparatively high specific activity but are unstable in the absence of a stabilizer. The enzyme derived from *Moraxella* sp. (J. Bacteriol., vol. 170, 3189, 1988; JP-A-63-313580) is low in specific activity and has a large Km value for formate. The enzyme derived from *Hyphomicrobium* sp. (JP-A-2000-78970, reported at 1999 Congress of Japan Society for Bioscience, Biotechnology, and Agrochemistry, Synopsis of Papers Read Before the same Congress, p. 234) is low in specific activity and has a low pH range for activity. Moreover, the enzyme derived from *Paracoccus* sp. (JP-A-03-61481) has a large Km value for formate.

A further problem is that while the products (e.g. haloalcohols) obtainable by reducing haloketone compounds are very useful compounds as raw materials of such as pharmaceutical products, the formate dehydrogenases heretofore reported are invariably inactivated in the presence of a haloketone compound so that if added to an enzymatic reduction reaction system for a haloketone compound, none are able to regenerate the coenzyme. Thus, there is not known a formate dehydrogenase capable of regenerating the coenzyme with good efficiency in the enzymatic reduction reaction system of a haloketone compound.

Referring to formate dehydrogenases of the bacterial origin, enzymes which do not require NAD as the electron acceptor [EC1.2.2.1]), such as those derived from *Escherichia coli* (J. Biol. Chem., vol. 250, 6693, 1975), *Clostridium pasteurianum* (J. Bacteriol., vol. 159, 375, 1984), *Clostridium thermoaceticum* (J. Biol. Chem., vol. 259, 1826, 1983), etc. are also known but these cannot be utilized for the purpose of regenerating the coenzyme NAD.

Referring to the expression of bacterial NAD-dependent formate dehydrogenase genes in transformants, the genes derived from *Pseudomonas* sp. 101 (Biotechnol. Appl. Biochem., vol. 18, 201, 1993), *Mycobacterium vaccae* (Appl. Microbiol. Biotechnol., vol. 44, 479, 1995, JP-A-10-23896), *Pyrococcus* KOD1 (JP-A-2000-69971), *Hyphomicrobium* sp. (JP-A-2000-78970, reported at the 1999 Congress of Japan Society for Bioscience, Biotechnology, and Agrochemistry, Synopsis of Papers Read Before the same Congress, p. 234) but there has been no knowing of a formate dehydrogenase gene derived from any microorganism of the genus *Thiobacillus*.

It is known that bacteria of the genus *Thiobacillus* have formate dehydrogenase activity in the form of crude enzyme solutions (J. Bacteriol., 131, 389 (1977)) but there is no report on the actual purification and isolation of an enzyme or on the characterization thereof, nor has it been reported that a relevant gene was ever isolated.

SUMMARY OF THE INVENTION

The present invention provides a formate dehydrogenase which is free from the above-mentioned disadvantages of the hitherto-known formate dehydrogenases, namely low enzyme productivity, low specific activity, large Km values for formate and NAD, narrow temperature and pH ranges of stability, and narrow pH range for action, but also has industrially useful characteristics such as high tolerance to haloketone compounds and a process for producing the same. The invention further provides a process for regenerating the coenzyme with good efficiency even in enzymatic reduction reaction systems, particularly in the enzymatic reduction of haloketone compounds which would inactivate the conventional formate dehydrogenases.

In view of the above state of the art, the inventors of the present invention did an extensive screening for soil microorganisms having formate dehydrogenase activity and, as a result, firstly isolated a strain of microorganism of the genus Thiobacillus which is capable of elaborating a formate dehydrogenase having laudable properties on a high production scale. From this strain of microorganism, the inventors isolated and purified the formate dehydrogenase and further succeeded in the isolation of a formate dehydrogenase gene and the expression of the gene in host microorganisms. Furthermore, it was found that the formate dehydrogenase of the invention is tolerant to haloketone compounds and capable of regenerating the coenzyme with good efficiency even in the enzymatic reduction system of a haloketone compound.

The present invention, therefore, is concerned with a polypeptide tolerant to haloketone compounds and having formate dehydrogenase activity.

The present invention is further concerned with a polypeptide,
which has the following physicochemical properties.
(1) Action: Using NAD as coenzyme, it oxidizes formates and produces carbon dioxide
(2) Molecular weight: $9 \times 10^4$, approx.
(3) Km value for formate: 1.6 mM
(4) Km value for NAD: 0.048 mM
(5) Temperature range for action: 20° C. to 65° C., optimum temperature 50° C. to 60° C.
(6) pH range for action: 5.0 to 10.5, optimum pH: 5.5 to 9.5
(7) Temperature range of stability: not over 50° C.
(8) pH range of stability: 4.5 to 9.0

The above polypeptide according to the invention is not only haloketone-tolerant but also has high specific activity, small Km values for formate and NAD, broad temperature and pH ranges of stability, broad temperature and pH ranges for action, and characteristics suited for industrial application all in one.

The present invention is further concerned with a polypeptide of the following (a) or (b):
(a) a polypeptide comprising an amino acid sequence shown under SEQ ID NO:1 of the sequence listing
(b) a polypeptide comprising an amino acid sequence derived from the amino acid sequence shown under SEQ ID NO:1 of the sequence listing by substitution, insertion, deletion and/or addition of one or several amino acids and having formate dehydrogenase activity.

The present invention is further concerned with a DNA coding for the above polypeptide.

The present invention is further concerned with a DNA of the following (c) or (d):
(c) a DNA comprising a base sequence shown under SEQ ID NO:2 of the sequence listing
(d) a DNA having a base sequence derived from a base sequence shown under SEQ ID NO:2 of the sequence listing by substitution, insertion, deletion and/or addition of one or several bases and coding for the polypeptide having formate dehydrogenase activity.

The present invention is further concerned with a DNA of the following (e) or (f):
(e) a DNA comprising a base sequence shown under SEQ ID NO:3 of the sequence listing
(f) a DNA having a base sequence derived from a base sequence shown under SEQ ID NO:3 of the sequence listing by substitution, insertion, deletion and/or addition of one or several bases and coding for the polypeptide having formate dehydrogenase activity.

The present invention is further concerned with a recombinant plasmid containing said DNA.

The present invention is further concerned with a transformant obtained by transforming a host microorganism with said recombinant plasmid.

The present invention is further concerned with a process for producing a formate dehydrogenase,
which comprises cultivating either a strain of microorganism capable of producing said polypeptide or said transformant to let it elaborate and accumulate said polypeptide in the resulting culture medium and harvesting the same.

In a further aspect, the present invention is concerned with a process for regenerating a coenzyme,
which comprises permitting either said polypeptide or a strain of microorganism capable of producing said polypeptide or a processed matter thereof to be present in an enzymatic reduction reaction system.

DETAILED DESCRIPTION OF THE INVENTION

The present invention is now described in detail.
The polypeptide of the invention is described in the first place. The polypeptide according to the invention is tolerant to haloketone compounds and has formate dehydrogenase activity.

Furthermore, the polypeptide of the invention is a polypeptide having formate dehydrogenase activity which is characterized by the following physicochemical properties.
(1) Action: Using NAD as coenzyme, it oxidizes formates and produces carbon dioxide
(2) Molecular weight: $9 \times 10^4$, approx.
(3) Km value for formate: 1.6 mM
(4) Km value for NAD: 0.048 mM
(5) Temperature range for action: 20° C. to 65° C., optimum temperature: 50° C. to 60° C.
(6) pH range for action: 5.0 to 10.5, optimum pH: 5.5 to 9.5
(7) Temperature range of stability: not over 50° C.
(8) pH range of stability: 4.5 to 9.0

In the present invention, the formate dehydrogenase activity of the polypeptide is assayed by quantitating the increase in absorbance at 340 nm resulting from the production of NADH at 30° C. or 40° C. in a 0.1 M phosphate buffer (pH 7) containing 500 mM sodium formate and 5 mM NAD.

The molecular weight determination is by gel permeation chromatography. The Km value for formate is determined by measuring the activity under the above conditions of activity assay (30° C., NAD 5 mM) while the concentration of sodium formate is varied, and the Km value for NAD is determined under the above conditions of activity assay (30° C., sodium formate 500 mM) while the concentration of NAD is varied.

The temperature for action and the pH for action are determined by measuring the activity while the temperature or pH is varied under the above conditions of activity assay. The temperature stability is evaluated by treating the polypeptide at each temperature for 10 minutes and measuring the residual activity. The pH stability is evaluated by treating the polypeptide at 30° C. for 22 hours at each pH level and measuring the residual activity.

The polypeptide of the invention is tolerant to haloketone compounds. The term "tolerant to haloketone compounds" as used in this specification means that the residual activity after 5 minutes' incubation of a crude enzyme solution at 30° C. in the presence of 10 mM ethyl 4-chloroacetoacetate is not less than 25%.

The polypeptide of the invention can be acquired from microorganisms having formate dehydrogenase activity. Therefore, as microorganisms for use as sources of the polypeptide of the invention, methanol-utilizing bacteria and formate-utilizing bacteria can be used with advantage. Thus, although this is not exclusive choices, microorganisms belonging to the genus *Thiobacillus*, for instance, can be used. In particular, *Thiobacillus* sp. are preferred and *Thiobacillus* sp. KNK65MA is especially preferred.

The *Thiobacillus* sp. KNK65MA mentioned above is the strain of microorganism which was isolated and obtained by the inventors of the present invention and has been deposited with the National Institute of Advanced Industrial Science and Technology International Patent Organism Depositary, Central 6, 1-1-1 Higashi, Tsukuba, Ibaraki, Japan as of Jul. 19, 2001 under the accession number of FERM BP-7671. The bacteriological characteristics of *Thiobacillus* sp. KNK65MA are shown below.

1. Morphology
    1) Bacilli ca 0.6 μm dia. × 1.5 to 2.0 μm
    2) Gram stain: negative
    3) Motility: non-motile
    4) Sporogenesis: non-sporulating
    5) Colonies on broth agar plate: round, smooth entire margin, low convex, lustrous, light yellow (translucent)
2. Cultural characteristics
    1) Broth liquid culture: suspended
    2) Litmuth milk: unchanged
3. Physiological characteristics
    1) Catalase: +
    2) Oxidase: +
    3) O/F test: −
    4) Denitrification: +
    5) MR test: +
    6) VP test: −
    7) Hydrogen sulfide production: −
    8) Utilization of citric acid
        Koser: −
        Christensen: −
    9) Utilization of inorganic nitrogen sources
        $NaNO_3$: −
        $(NH_4)_2SO_4$: −
    10) Starch hydrolysis: −
    11) Nitrate reduction: −
    12) Indole production: −
    13) Glucose acidification: −
    14) Arginine dihydrolase: −
    15) Urease: −
    16) β-galactosidase: +
    17) Esculin hydrolysis: +
    18) Gelatin hydrolysis: −
    19) Range for growth
        pH
            3.0: −
            5.0: −
            8.0: +
        Temperature (° C.)
            30: +
            50: −
    20) Biotin requirement: +
    21) Anaerobic growth: +
    22) Utilization of sulfur compounds
        Elemental sulfur: −
        Sodium thiosulfate: +
    23) Ethanol oxidation: $+_w$
    24) Acid and gas production from carbohydrates in O—F medium (acid/gas)
        L-arabinose: −/−
        D-glucose: −/−
        D-fructose: −/−
        Maltose: −/−
        Lactosse: −/−
        D-sorbitol: −/−
        Inositol: −/−
        Starch: −/−
        D-xylose: −/−
        D-mannose: −/−
        D-galactose: −/−
        Sucrose: −/−
        Trehalose: −/−
        D-mannitol: +/−
        Glycerol: −/−
    25) Substrate utilization
        Glucose: +
        L-arabinose: −
        D-mannose: −
        D-mannitol: +
        N-acetyl-D-glucosamine: −
        Maltose: −
        Potassium gluconate: +
        n-Capric acid: −
        Adipic acid: −
        dl-Malic acid: −
        Sodium citrate: −
        Phenyl acetae: −

As the medium for cultivating a microorganism producing the polypeptide of the invention, an aqueous medium containing methanol as a major carbon source together with nitrogen sources and nutrients such as inorganic salts is used. Satisfactory results are obtained in many cases when organic trace nutrients such as vitamins and amino acids are added. As the nitrogen sources, ammonium salts, aqueous ammonia, ammonia gas, urea, yeast extract, peptones, corn steep liquor, etc. can be used. As the inorganic salts, phosphates, magnesium salts, potassium salts, sodium salts, calcium salts, iron salts, sulfates, and chlorides can be used.

Culture can be made generally within the temperature range of 20° C. to 40° C., preferably at 20° C. to 30° C. The cultivation pH may range from 6.0 to 9.0, and is preferably from 7.0 to 9.0. The cultural process may be continuous or batch-wise.

Regarding the separation and purification from the culture medium, the cells are harvested, for example by centrifuging the culture medium, at completion of culture and disrupted, for example by sonication, to recover a crude enzyme solution. The polypeptide of the invention can be obtained by purifying the crude enzyme solution by salting-out or column chromatography, for instance.

The polypeptide of the invention may be a native enzyme acquired from a microorganism as above or a recombinant enzyme as produced by utilizing the recombinant gene technology.

As the native enzyme, the polypeptide shown under SEQ ID NO:1 of the sequence listing can be mentioned.

The polypeptide of the invention may also be a polypeptide comprising an amino acid sequence derived from the amino acid sequence shown under SEQ ID NO:1 by substitution, insertion, deletion and/or addition of one or several amino acids and having formate dehydrogenase activity.

The "amino acid sequence derived by substitution, insertion, deletion and/or addition of one or several amino acids" can be acquired by the-technology well known to those skilled in the art, such as the method of site-specific mutagenesis, through said substitution, insertion, deletion and/or addition of one or several amino acids. Specific relevant protocols are described in Nucleic Acid Res. 10, 6487 (1982), Methods in Enzymology 100, 448 (1983), among other literature.

The term "polypeptide having formate dehydrogenase activity" means any polypeptide showing at least 10%, preferably not less than 40%, more preferably not less than 60%, still more preferably not less than 80%, of the activity of the polypeptide comprising the amino acid sequence shown under SEQ ID NO:1 when determined under the above conditions of activity assay.

Now, the DNA according to the invention is described. The DNA of the invention may be any DNA that codes for a polypeptide such as the one described above. It may for example be a DNA comprising the base sequence shown under SEQ ID NO:2 or SEQ ID NO:3 of the sequence listing. Furthermore, it may be any DNA having a base sequence derived from the base sequence shown under SEQ ID NO:2 or SEQ ID NO:3 by substitution, insertion, deletion and/or addition of one or several bases and coding for a polypeptide having formate dehydrogenase activity.

The "base sequence derived by substitution, insertion, deletion, and/or addition of one or several bases" means a base sequence derived by substitution, insertion, deletion and/or addition of such a number of bases as can be substituted, inserted, deleted and/or added by the technology well known to those skilled in the art as described in, inter alia, Supplemental Issue, Tanpakushitsu, Kakusan, Koso (Protein, Nucleic Acid and Enzyme), PCR Method for Gene Amplification, TAKKAJ, 35 (17), 2951-3178 (1990) or Henry A. Erlich (ed.), translated into Japanese under the supervision of Ikunoshin Kato: PCR Technology (1990).

Furthermore, it may be a DNA which hybridizes with a DNA comprising the base sequence shown under SEQ ID NO:2 or SEQ ID NO:3 under stringent conditions and coding for a polypeptide having formate dehydrogenase activity.

The "DNA which hybridizes with a DNA comprising the base sequence shown under SEQ ID NO:2 or SEQ ID NO:3 under stringent conditions" means a DNA which can be acquired by the colony hybridization, plaque hybridization, Southern hybridization, or the like technique using a DNA comprising the base sequence shown under SEQ ID NO:2 or 3 as a probe. Any one skilled in the art may easily carry out such hybridization procedures in accordance with the protocols described in Molecular Cloning 2nd Edt. (Cold Spring Harbor Laboratory Press, 1989) to acquire the objective DNA.

The DNA (formate dehydrogenase gene) according to the invention can be acquired from said microorganism having formate dehydrogenase activity. The objective DNA may be acquired by, inter alia, the following method.

In the first place, the amino acid sequence at the amino-terminus of a formate dehydrogenase purified from a strain of microorganism having formate dehydrogenase activity is determined by means of a gas-phase protein sequencer, for instance. The DNA primer designed on the basis of this amino acid sequence and the DNA primer designed on the basis of the sequence of high homology among the base sequences of known formate dehydrogenase genes are synthesized.

Then, from the source microorganism for formate dehydrogenase, the chromosomal DNA is isolated. The chromosomal DNA can be acquired by lysing and extracting cultured cells with a surfactant, CTAB, chloroform, phenol and the like, causing the extracted DNA to be precipitated from isopropyl alcohol, centrifuging the same, and washing the resulting DNA pellet with ethanol (e.g. Current Protocols in Molecular Biology (Greene Publishing Associates and Wiley-Interscience)).

Part of the objective gene can be obtained by carrying out PCR using this chromosomal DNA as a template and the above primers. Then, to acquire the full length of the objective gene, the chromosomal DNA obtained above is digested with suitable restriction enzymes such as HindIII and EcoRI and subjected to agarose electrophoresis. Using the DNA fragment which is part of the above formate dehydrogenase gene obtained by PCR as a probe, Southern hybridization is carried out and the DNA fragment containing the formate dehydrogenase gene and not cleaved by said restriction enzymes within the formate dehydrogenase gene is detected on the gel.

This DNA fragment is recovered from the gel and cyclized with e.g. T4 DNA ligase and using the resulting DNA as a template and synthetic DNA primers based on the base sequences corresponding to enzyme N-terminal and C-terminal regions of the partial formate dehydrogenase gene obtained by PCR as above and directed outwardly of said enzyme gene, PCR is carried out to construct DNA fragments coding for the further N-terminal and C-terminal sides of the partial gene already acquired with above primers. After sequencing of the DNA fragments, DNA primers are constructed based on the base sequences of the DNAs deduced to be present upstream of the DNA coding for the N-terminus and downstream of the DNA coding for the C-terminus of the enzyme and the DNA between these sequences is amplified to acquire a DNA fragment containing the full-length formate dehydrogenase gene. The acquired DNA fragment can be confirmed to contain the full length of the objective formate dehydrogenase gene by determination of molecular weight and partial base sequence analysis.

Then, the DNA fragment containing the formate dehydrogenase gene as obtained above can be integrated into a vector DNA with e.g. T4 DNA ligase to construct a recombinant plasmid. Using this plasmid, the DNA fragment containing the formate dehydrogenase gene inserted into the vector is sequenced to confirm the presence of bases coding for the N-terminal amino acid sequence of the formate dehydrogenase. In addition, the site of translation initiation is determined and using the sequence down to the termination codon as an open reading frame, it is confirmed that this base sequence has relatively high homology with the known formate dehydrogenase gene, the encoded protein corresponds to the molecular weight determined by electrophoresis, etc., whereby the product is identified to be the objective gene.

By transforming a host strain of microorganism with the DNA thus acquired or a recombinant plasmid constructed by integrating this DNA into a vector, a transformant can be obtained.

As the host and vector, the host-vector systems described in "Recombinant DNA Experimentation Guidelines" (edited by Life Science Section, Research and Development Bureau of Science and Technology Agency, Japan, as amended Mar. 22, 1996) can be utilized. For example, the host which can be used includes microorganisms belonging to any of the following genera: *Escherichia, Pseudomonas, Flavobacterium, Bacillus, Serratia, Corynebacterium, Brevibacterium, Agrobacterium, Acetobacter, Gluconobacter, Lactobacillus, Streptococcus*, and *Streptomyces*, among others. As the vector, plasmids and phages of the microbial origin, inclusive of derivatives thereof, which are capable of autonomous replication within these hosts can be employed. The particularly preferred host microorganism is *Escherichia coli* and the suitable vector is one capable of autonomous replication in this microorganism. Among such vectors are pUC18, pUC19, pBR322, pACYC184, pSC101, and pUCNT.

Referring to said transformant, the recombinant plasmid pFT001 constructed by integrating the above-acquired DNA into the pUC19 vector or the recombinant plasmid pFT002 constructed by integrating the same into pUCNT (WO 94/03613), can be used to transform *Escherichia coli* HB101 to give the trnasformant *Escherichia coli* HB101 (pFT001) or *Escherichia coli* HB101 (pFT002). The recombinant plasmid pFT001 is shown in FIG. 1 and the recombinant plasmid pFT002 is shown in FIG. 2.

The above transformants *Escherichia coli* HB101 (pFT001) and *Escherichia coli* HB101 (pFT002) according to the invention have been deposited with the National Institute of Advanced Industrial Science and Technology International Patent Organism Depositary, Central 6, 1-1-1 Higashi, Tsukuba, Ibaraki, Japan as of Jul. 19, 2001 under the accession number of FERM BP-7672 and as of Jul. 19, 2001 under the accession number of FERM BP-7673, respectively.

For increasing the enzyme output, a vector modified to have a potent structural promoter can be employed.

The recombinant DNA technology used in the present invention is well-known in the art and has been described, inter alia, in Molecular Cloning 2nd Edition (Cold Spring Harbor Laboratory Press, 1989), Current Protocols in Molecular Biology (Greene Publishing Associates and Wiley-Interscience).

The process for producing a formate dehydrogenase according to the invention is characterized in that a strain of microorganism capable of producing the above-described polypeptide is cultivated to let it elaborate and accumulate said polypeptide in the resulting culture medium and the polypeptide so accumulated is harvested.

The process for producing a formate dehydrogenase according to the invention is characterized in that said transformant is cultivated to let it elaborate and accumulate a formate dehydrogenase in the resulting culture medium and the formate dehydrogenase so accumulated is harvested.

The production of a formate dehydrogenase using the transformant according to the invention can be carried out by cultivating the transformant in a common medium. The medium for use to cultivate may be a common medium containing source of carbon, source of nitrogen and nutrients such as inorganic salts. Superior results are frequently obtained when organic trace nutrients such as vitamins and amino acids are further formulated. As the carbon source, carbohydrates such as glucose and sucrose, organic acids such as acetic and other acids, and alcohols can be judiciously used. As the nitrogen source, ammonium salts, aqueous ammonia, ammonia gas, urea, yeast extract, peptones, corn steep liquor, etc. can be utilized. As said inorganic salts, various phosphates, magnesium salts, potassium salts, sodium salts, calcium salts, iron salts, sulfates, and chlorides can be used.

Culture can be made within the temperature range of 25° C. to 40° C., although the range of 25° C. to 37° C. is particularly preferred. The cultivation pH may range from 4 to 8 and is preferably from 5 to 7.5. The cultural process may be continuous or batch-wise.

Where necessary, an enzyme induction treatment such as addition of methanol, formic acid, isopropyl-1-thio-β-D-galactoside (IPTG), lactose, or the like may be carried out.

Regeneration of the coenzyme can be achieved by permitting either said polypeptide or a strain of microorganism capable of producing the polypeptide or a processed matter thereof to be present in the enzymatic reduction reaction system.

Thus, by permitting the formate dehydrogenase of the invention to be present in an enzymatic reduction reaction system, the coenzyme can be regenerated with good efficiency. Particularly, the coenzyme can be efficiently regenerated in the presence of this enzyme even in the enzymatic reduction system of a haloketone compound or the like which would inactivate the conventional formate dehydrogenase.

For example, the enzymatic reduction reaction of a haloketone such as ethyl 4-chloroacetoacetate using the formate dehydrogenase of the invention for coenzyme regeneration can be carried out as follows.

This reaction can be carried out in water or a suitable organic solvent which is hardly soluble in water, for example ethyl acetate, butyl acetate, toluene, chloroform or n-hexane, or a biphasic system consisting of such an organic solvent and an aqueous medium. The reaction can be achieved by adding to such a solvent a substrate haloketone, the coenzyme NAD, and either a haloketone reductase or a microorganism having such reductive activity or a processed matter thereof, and either the polypeptide (i.e. haloketone-tolerant formate dehydrogenase) of the invention or a microorganism capable of producing this polypeptide or a processed matter thereof and stirring the mixture under judicious pH control with formic acid.

The haloketone compound is not particularly restricted provided that it can be a substrate for the reductase and microorganism to be used, thus including ethyl 4-chloroacetoacetate, ethyl 4-bromoacetoacetate, ethyl 4-iodoacetoacetate, methyl 4-chloroacetoacetate, ethyl 2-chloroacetoacetate, 2-chloro-1-(3-pyridinyl)ethanone, 1,1-dimethylethyl [(1S)-3-chloro-2-oxo-1-(phenylmethyl)propyl]carbamate, 2-chloroacetophenone, 2,3'-dichloroacetophenone, chloroacetone, 1-(benzoyloxy)-3-chloro-2-propanone, and 1-chloro-3-hydroxy-2-propanone, among others. The preferred substrates are α-haloketones such as ethyl 4-chloroacetoacetate, methyl 4-chloroacetoacetate, ethyl 2-chloroacetoacetate, 1,1-dimethylethyl [(1S)-3-chloro-2-oxo-1-(phenylmethyl)propyl]carbamate, 2,3'-dichloroacetophenone, and 1-(benzoyloxy)-3-chloro-2-propanone.

As said reductase or microorganism capable of reducing a haloketone, the recombinant *Escherichia coli* HB101 (pNTS1M1) (FERM BP-8059) capable of reducing ethyl 4-chloroacetoacetate to a corresponding alcohol, for instance, can be employed. This recombinant *E. coli* HB101 (pNTS1M1) strain was originally deposited with the National Institute of Advanced Industrial Science and Technology, 1-1-1 Higashi, Tsukuba, Ibaraki, Japan as of Jun. 22, 2001 and transferred to the Budapest Treaty depositry as of May 27, 2002 with the accession number of FERM BP-8059 being assigned. It is to be understood that when an aldehyde dehydrogenase or an amino acid dehydrogenase, or a microorganism having the corresponding activity or a processed matter thereof is used as the reductase, a corresponding aldehyde or amine can be obtained as the product.

As the microorganism capable of producing the polypeptide of the invention, the above-mentioned transformant *Escherichia coli* HB101 (pFT001) or *Escherichia coli* HB101 (pFT002), for instance, can be employed.

The term "processed matter" as used herein with reference to said microorganism means any of the crude extract, lyophilized preparation and acetone-dried preparation of cultured cells, or a ground matter of such cells. Furthermore, these may be used in the form of the enzyme or cells immobilized in the conventional manner. The immobilization can be effected by various techniques known to those skilled in the art (e.g. crosslinking, physical adsorption, entrapment, etc.).

The reaction is carried out at 10° C. to 70° C., preferably 20° C. to 60° C., and at pH 4 to 10, preferably pH 5.5 to 9.5. The substrate concentration of the charge is 0.1% to 90% (w/v) but the substrate may be supplied continuously. The reaction can be carried out batch-wise or continuously. The reaction of the invention can be conducted by utilizing the immobilized enzyme, a membrane reactor, and/or other contrivances.

As described above, the method of the invention is such that in the reduction reaction for enzymatic production of ethyl 4-chloro-3-hydroxybutyrate and other alcohols, amines, aldehydes, or the like, it provides for efficient coenzyme regeneration contributing to a drastic reduction in the level of use of an expensive coenzyme.

BEST MODES FOR CARRYING OUT THE INVENTION

Figure 1:
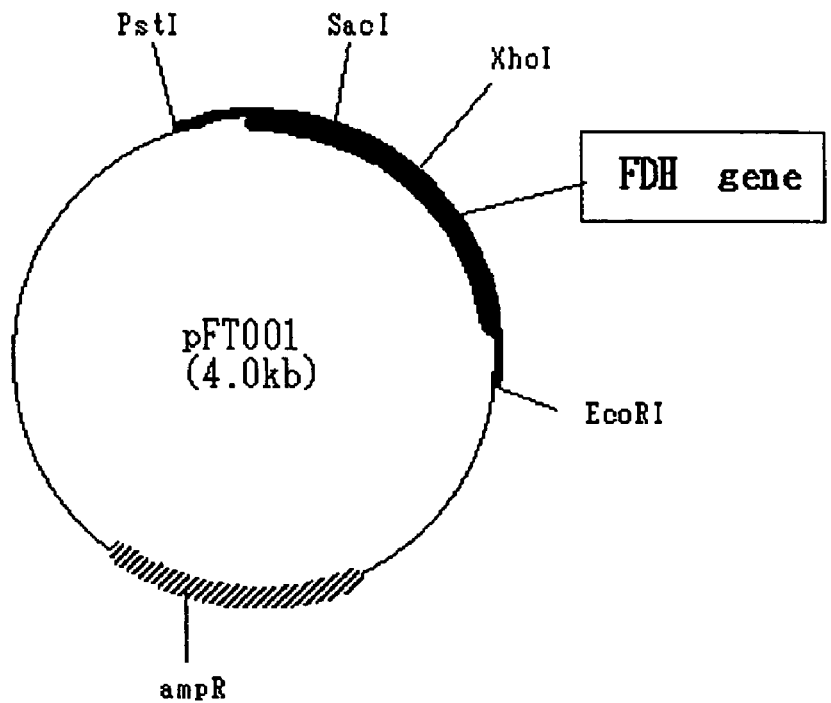
FIG. 1 is a restriction enzyme map of the recombinant plasmid pFT001 containing the formate dehydrogenase gene of the invention.

The following examples illustrate the present invention in further detail. It should, however, be understood that the invention is by no means restricted by these examples.

EXAMPLE 1

Acquisition of the *Thiobacillus* sp. KNK65MR Strain

The formate dehydrogenase high-producer strain of the invention, namely *Thiobacillus* sp. KNK65MA, was isolated as follows. Soil samples collected from various geographic locations were respectively suspended in 0.9% saline. Each of the supernatants obtained in size of 1% was inoculated into 7 ml of the liquid medium of the composition shown in Table 1, which contained methanol as a sole carbon source, followed by shake culture at 30° C. under aerobic conditions.

TABLE 1

| | |
|---|---|
| Methanol | 8 g |
| $(NH_4)_2SO_4$ | 5 g |
| $KH_2PO_4$ | 0.15 g |
| $K_2HPO_4$ | 4.85 g |
| $MgSO_4$ | 0.5 g |
| NaCl | 0.1 g |
| $CaCl_2$ | 0.1 g |
| Meat extract | 0.1 g |
| Yeast extract | 0.1 g |
| Polypeptone | 0.1 g |
| Biotin | 20 µg |
| Calcium pantothenate | 2 mg |
| Folic acid | 2 µg |
| Inositol | 10 mg |
| Niacin | 400 µg |
| p-aminobenzoic acid | 200 µg |
| Pyridoxine hydrochloride | 400 µg |
| Riboflavin | 200 µg |
| Thiamin hydrochloride | 400 µg |
| Boric acid | 500 µg |
| $CuSO_4$ | 40 µg |
| KI | 100 µg |
| $FeCl_3$ | 200 µg |
| $MnSO_4$ | 400 µg |
| $Na_2MoO_4$ | 200 µg |
| $ZnSO_4$ | 400 µg |

The above composition was made up to 1 L with water, adjusted to pH 9, sterilized by autoclaving, and used. However, methanol was added after sterilization.

Each culture medium showing bacterial growth was analyzed for cell concentration in terms of absorbance at 600 nm. The cells obtained by centrifuging 1.5 ml of the above culture medium was suspended in 0.5 ml of a substrate solution (0.1 M phosphate buffer, 0.5 M sodium formate, 1 mM NAD, 1% Triton X-100, pH 7) and shake-cultured at 30° C. for 20 hours for cellular reaction. The reaction mixture was centrifuged and the amount of NADH in the supernatant was determined at 340 nm. The strain giving a high quotient when the NADH output was divided by cell concentration was selected as a strain having high formate dehydrogenase activity. Then, 5 ml of the culture medium of the selected strain was centrifuged and the resulting cells was suspended in 0.5 ml of 0.1 M phosphate buffer (pH 7), sonicated, and centrifuged to obtain a crude enzyme solution as supernatant.

The formate dehydrogenase activity of the crude enzyme solution was assayed by quantitating the increase in absorbance at 340 nm resulting from production of NADH in 0.1 M phosphate buffer (pH 7) containing 500 mM sodium formate and 5 mM NAD at 30° C.

Protein assays were carried out by the method of Bradford (Anal. Biochem., vol. 72, 248, 1976) using BSA as standard protein.

The α-haloketone tolerance of the formate dehydrogenase was evaluated by mixing 150 µl of the crude enzyme solution with 150 µl of 20 mM ethyl 4-chloroacetoacetate, incubating the mixture at 30° C. for 5 minutes, assaying formate dehydrogenase activity in the same manner as above, and comparing the result with the pre-treatment activity.

Then, in cases where the specific activity of the crude enzyme solution was high and the tolerance to ethyl 4-chloroacetoacetate was high, the strain having formate dehydrogenase activity was isolated from the culture medium by the monocolony method and the isolated strain of cells thus obtained were cultivated to prepare a crude enzyme solution in the same manner as above and the solution was analyzed for formate dehydrogenase activity, protein concentration, and haloketone tolerance. Then, a comparison of specific activity and haloketone tolerance of the crude enzyme solution was carried out for each strain of cells and accordingly *Thiobacillus* sp. KNK65MA (FERM BP-7671) was elected as a high producer of formate dehydrogenase with high specific activity and high haloketone tolerance.

EXAMPLE 2

Isolation and Purification of the Formate Dehydrogenase

A colony of *Thiobacillus* sp. KNK65MA was inoculated into 7 ml of a medium of the composition shown in Table 2 and shake-cultured aerobically at 28° C. for 2 days. The resulting culture medium each in size of 1% based on the medium volume was inoculated into 100 ml per flask of a production medium of the composition shown in Table 3 and shake-cultured aerobically at 28° C. for 7 days.

TABLE 2

| | |
|---|---|
| Methanol | 20 g |
| Glycerol | 10 g |
| Tryptone | 10 g |
| Yeast extract | 5 g |
| NaCl | 5 g |

The composition was made up to 1 L with water, adjusted to pH 7, sterilized by autoclaving, and used. However, methanol was added after sterilization.

TABLE 3

| | |
|---|---|
| Methanol | 20 g |
| $(NH_4)_2SO_4$ | 5 g |
| $KH_2PO_4$ | 0.15 g |
| $K_2HPO_4$ | 4.85 g |
| $MgSO_4$ | 0.5 g |
| NaCl | 0.1 g |
| $CaCl_2$ | 0.1 g |
| Meat extract | 0.1 g |

TABLE 3-continued

| | |
|---|---|
| Yeast extract | 0.1 g |
| Polypeptone | 0.1 g |
| Biotin | 20 μg |
| Calcium pantothenate | 2 mg |
| Folic acid | 2 μg |
| Inositol | 10 mg |
| Niacin | 400 μg |
| p-Aminobenzoic acid | 200 μg |
| Pyridoxine hydrochloride | 400 μg |
| Riboflavine | 200 μg |
| Thiamin hydrochloride | 400 μg |
| Boric acid | 500 μg |
| $CuSO_4$ | 40 μg |
| KI | 100 μg |
| $FeCl_3$ | 200 μg |
| $MnSO_4$ | 400 μg |
| $Na_2MoO_4$ | 200 μg |
| $ZnSO_4$ | 400 μg |

The composition was made up to 1 L with water, adjusted to pH 9, sterilized by autoclaving, and used. However, methanol was added after sterilization.

After completion of cultivation, the cells were harvested by centrifugation and suspended in 0.1 M phosphate buffer (pH 7.0) containing 1 mM dithiothreitol (DTT) and EDTA. The suspension was sonicated to disrupt the cells and centrifuged. The supernatant was salted out with 25 to 60% saturation of ammonium sulfate and the precipitate was recovered by centrifugation. This fraction was dissolved in 0.01 M phosphate buffer (pH 6.5) containing 1 mM DTT and EDTA and the solution was dialyzed against the same buffer. Then, DEAE-Sepharose (product of Pharmacia) column chromatography was carried out and after the column was washed with the same buffer, elution was carried out with 0.1 M phosphate buffer (pH 6.5) containing 1 mM DTT and EDTA. Active fractions were pooled and, after addition of ammonium sulfate to 24% saturation, applied to a chromatographic column of TSKgel Phenyl Toyopearl 650 M (product of Tosoh Corporation) and elution was carried out on an ammonium sulfate gradient of 24 to 0% saturation in 0.1 M phosphate buffer (pH 6.5) containing 1 mM DTT and EDTA. After addition of ammonium sulfate at a final concentration of 70% saturation to the active fractions, the pellet obtained by centrifugation was dissolved in 0.01 M phosphate buffer (pH 6.5) containing 1 mM DTT and EDTA, followed by dialysis against the same buffer. After this dialysis, the resulting material was applied to a chromatographic column of Blue Sepharose 6 Fast Flow (product of Pharmacia) and after the column was washed with the same buffer, elution was carried out on a NaCl gradient of 0.5 M to 0 M in the same buffer. The active fractions were pooled, concentrated with an ultrafiltration membrane (cut-off molecular weight 10,000), and dialyzed against 0.01 M phosphate buffer (pH 6.5) containing 1 mM DTT and EDTA. The resulting material was applied to a column of Gigapite (product of Seikagaku Corporation) for chromatography. After the column was washed with 2 mM phosphate buffer (pH 6.5) containing 1 mM DTT and EDTA, elution was carried out with 50 mM phosphate buffer (pH 6.5) containing 1 mM DTT and EDTA. The active fractions were pooled and analyzed by SDS-polyacrylamide electrophoresis. As a result, the formate dehydrogenase was detected as a single band, attesting to the high purity of the thus-purified enzyme.

EXAMPLE 3

Properties of the Enzyme

The properties of the purified formate dehydrogenase obtained in Example 2 were studied as follows.

[Specific Activity]

The activity of the formate dehydrogenase obtained was assayed by quantitating the increase in absorbance at 340 nm resulting from formation of NADH in 0.1 M phosphate buffer (pH 7) containing 500 mM sodium formate and 5 mM NAD at 30° C. or 40° C. In this connection, the amount of the enzyme yielding 1 mmol of NADH in 1 minute was defined as 1 unit. Protein assay was performed by the method of Lowry using BSA as standard protein. The specific activity of the purified formate dehydrogenase was 7.6 u/mg protein (30° C.) or 13.3 μ/mg protein (40° C.)

[Determination of Km Values]

Figure 3:
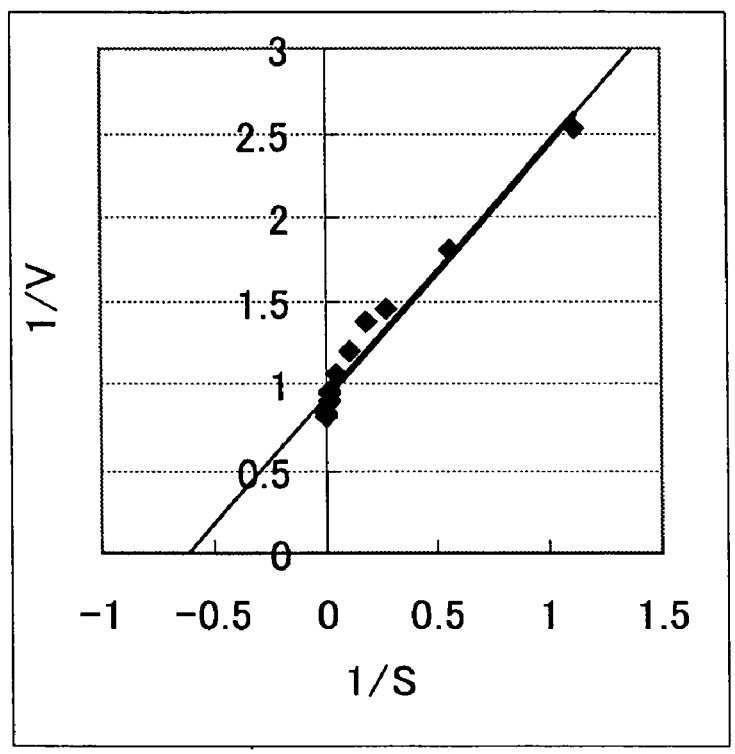
FIG. 3 is a graph for determining the Km value for formate of the formate dehydrogenase of the invention.
Figure 4:
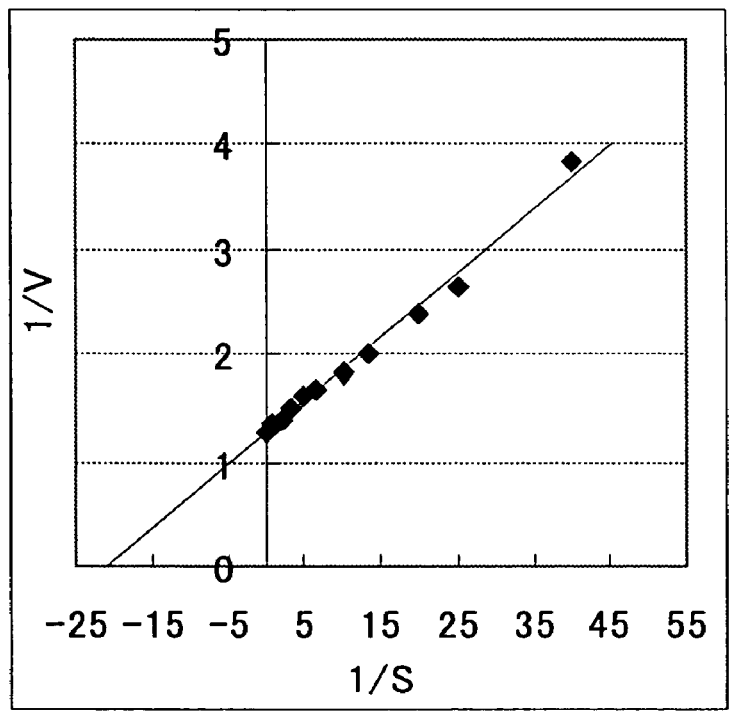
FIG. 4 is a graph for determining the Km value for NAD of the formate dehydrogenase of the invention.

The Km values for formate and NAD were determined as follows. Thus, the Km value for formate was determined by measuring the activity with the concentration of sodium formate varied under the above specific activity assay conditions (30° C., NAD 5 mM) and the Km value for NAD was determined by measuring the activity with the concentration of NAD varied under the above specific activity assay conditions (30° C., sodium formate 500 mM). In FIG. 3 and FIG. 4, V represents the reaction velocity of the enzyme, S represents the concentration of the substrate, and the intercept of the abscissa represents $-1/Km$. The Km value for formate is found from FIG. 3 to be 1.6 mM and that for NAD is found from FIG. 4 to be 0.048 mM.

[Temperature Range for Action and Optimum Temperature]

Figure 5:
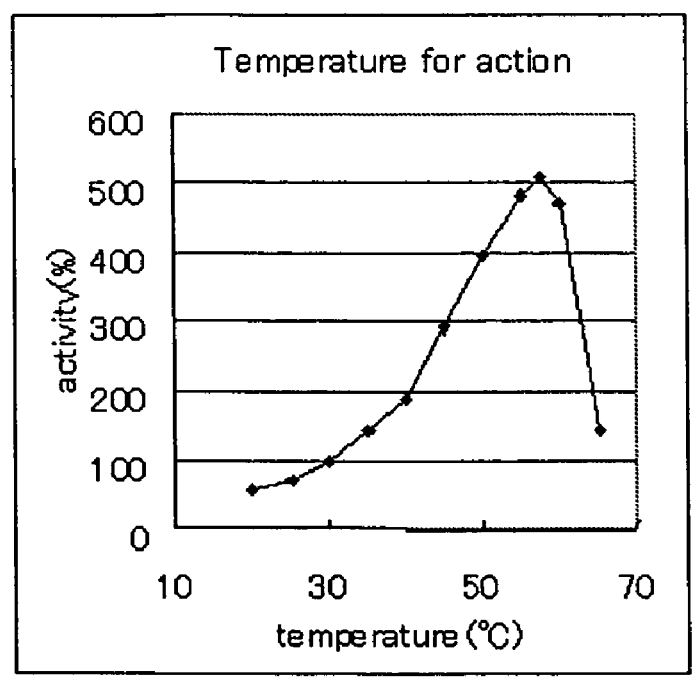
FIG. 5 is a graph for determining the temperature range for action and optimum temperature of the formate dehydrogenase of the invention.

The temperature range for action and optimum temperature were investigated. FIG. 5 is a graph showing the relative activity at each temperature level, with the activity at 30° C. being taken as 100%. It should be understood that the pH was kept constant at 7 for all temperatures. The enzyme of the invention acted well within the range of 20° C. to 65° C., with the optimum temperature being 50° C. to 60° C.

[pH Range for Action and Optimum pH]

Figure 6:
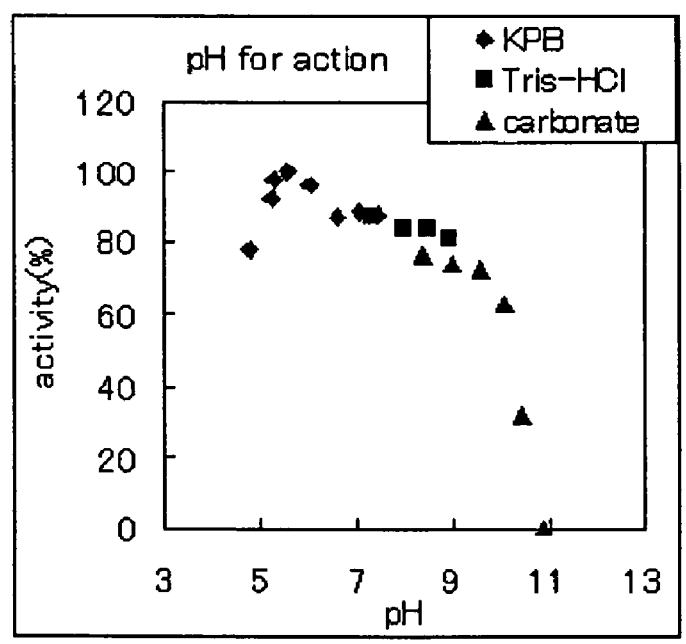
FIG. 6 is a graph for determining the pH range for action and optimum pH of the formate dehydrogenase of the invention.

The pH range for action and optimum pH were investigated. FIG. 6 is a graph showing the relative activity at each pH level, with the activity at pH 5.6 being taken as 100%. It should be understood that the temperature was kept constant at 30° C. for all pH levels. The enzyme of the invention acted well within the range of pH 5.0 to 10.5, with the optimum pH being 5.5 to 9.5.

[Temperature Stability]

Figure 7:
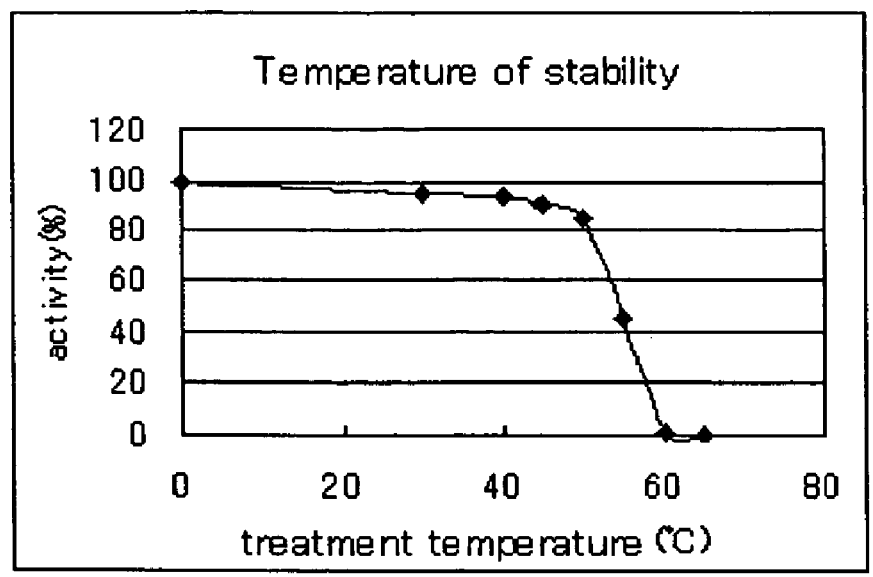
FIG. 7 is a graph for determining the temperature stability of the formate dehydrogenase of the invention.

The temperature stability was investigated. FIG. 7 is a graph constructed by plotting residual activity after 10 minutes' treatment at each temperature in 0.1 M phosphate buffer (pH 7), with the activity at 0° C. being taken as 100%. The enzyme of the invention was stable at temperatures not over 50° C.

[pH Stability]

Figure 8:
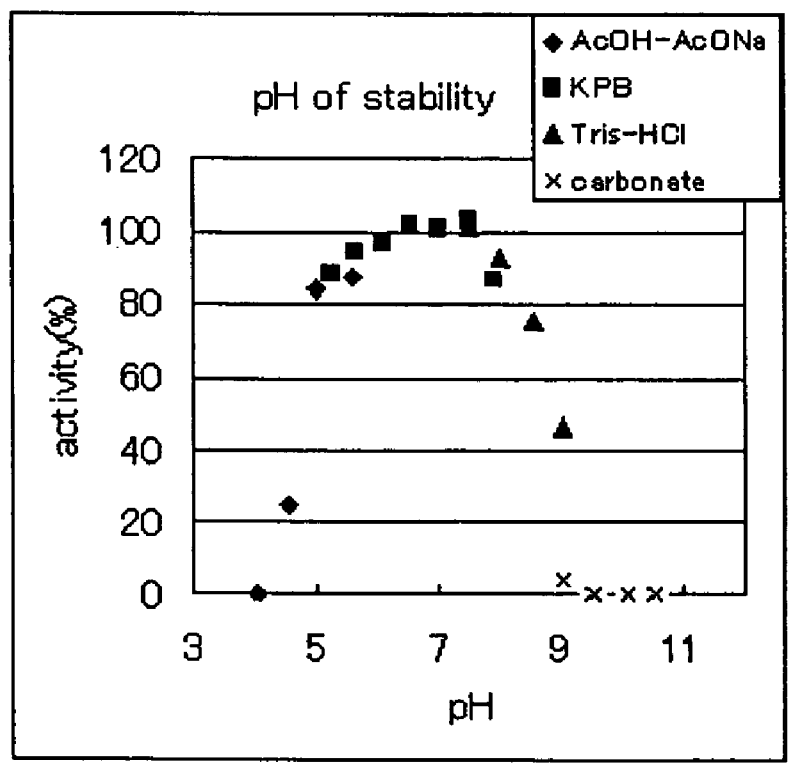
FIG. 8 is a graph for determining the pH stability of the formate dehydrogenase of the invention.

The pH stability was investigated. FIG. 8 is a graph constructed by plotting residual activity after 22 hours' treatment at 30° C. with pH varied, with the activity at pH 7.5 being taken as 100%. The enzyme of the invention was comparatively stable within the range of pH 4.5 to 9.0.

[Molecular Weight Determination]

As determined by gel permeation chromatography, the molecular weight was approximately $9 \times 10^4$ ($9 \times 10^4 \pm 5 \times 10^3$).

EXAMPLE 4

Isolation of the Formate Dehydrogenase Gene

In the first place, the cells obtained by cultivating *Thiobacillus* sp. KNK65MA in the same manner as in Example 1 were lysed and extracted with a surfactant, CTAB, chloroform, phenol and the like, and the extracted DNA was precipitated from isopropyl alcohol and centrifuged. The DNA obtained as a pellet was washed with ethanol to give the chromosomal DNA (Current Protocols in Molecular Biology (Greene Publishing Associates and Wiley-Interscience)). To acquire the objective formate dehydrogenase gene, the amino-terminal amino acid sequence of the purified formate dehydrogenase was determined with a gas-phase protein sequencer or the like, and using the DNA mix primer (Primer-1) shown under SEQ ID NO:4 of the sequence listing as designed based on the above amino acid sequence and the DNA mix primer (Primer-2) shown under SEQ ID NO:5 of the sequence listing as designed based on the sequence of high homology among the base sequences of known formate dehydrogenase genes, a PCR using the above-obtained chromosomal DNA as a template was carried out. Referring to SEQ ID NO:4 and NO:5 of the sequence listing, n represents adenine, guanine, cytosine or thymine, r represents adenine or guanine, and y represents cytosine or thymine. As the result of PCR, part of the objective formate dehydrogenase gene was obtained. Then, to acquire the full length of the objective gene, the previously obtained-chromosomal DNA fragments digested by the restriction enzymes SacI, XbaI, HindIII, ClaI, BamHI, PstI and EcoRI was electrophoresed on agarose gel and Southern hybridization was carried out using DNA fragments of the partial formate dehydrogenase gene obtained by PCR as probes. As a result, it was the band containing the formate dehydrogenase gene which was detected in the case of EcoRI or HindIII digestion that showed that the formate dehydrogenase gene was not cleaved by the restriction enzyme as used and the DNA fragment containing the formate dehydrogenase gene was small. After recovery of these DNA fragments from the gels, cyclization was performed with T4 DNA ligase and using the resulting DNA derived from the EcoRI or HindIII digest as a template, the DNA primers (Primer-3, Primer-4) shown under SEQ ID NO:6 and NO:7 of the sequence listing directed outwardly of the enzyme gene were synthesized based on the base sequences corresponding to segments on the N-terminal and C-terminal sides, respectively, of the enzyme of the partial formate dehydrogenase gene obtained by PCR as above, and inverse PCR was carried out. Thus acquired was a DNA fragment containing outward gene segments not possessed by the partial gene obtained previously. After determination of the base sequence of this DNA fragment, using a DNA primer (Primer-5) having the sequence corresponding to the base sequence deduced to be situated upstream of the DNA encoding the N-terminus of the enzyme shown under SEQ ID NO:8 of the sequence listing and a restriction enzyme PstI restriction site combined thereto and a DNA primer (Primer-6) having the sequence corresponding to the base sequence deduced to be situated downstream of the DNA encoding the C-terminus shown under SEQ ID NO:9 of the sequence listing and a restriction enzyme EcoRI restriction site combined thereto, the DNA between these flanking regions was amplified by PCR to give a DNA fragment (SEQ ID NO:2 of the sequence listing) cotaining the full length of the formate dehydrogenase gene. Based on determination of molecular weight and analysis of partial base sequence of the DNA fragment thus obtained, the fragment was confirmed to contain the full length (SEQ ID NO:3 of the sequence listing) of the formate dehydrogenase gene.

EXAMPLE 5

Construction of a Recombinant Plasmid Containing the Formate Dehydrogenase Gene and Analysis of the Gene The DNA fragment containing the formate dehydrogenase gene as acquired in Example 4 was cleaved with restriction enzymes PstI and EcoRI and, using T4 DNA ligase, combined to the vector plasmid pUC19 cleaved with the same enzymes to construct a recombinant plasmid pFT001 containing the formate dehydrogenase gene as represented by the restriction enzyme map in FIG. 1. In FIG. 1, "FDH gene" represents the formate dehydrogenase gene of the invention.

Using the plasmid pFT001 thus acquired, the DNA fragment flanked by PstI and EcoRI sites as obtained in Example 4 was analyzed for base sequence. As a result, the presence of bases coding for the N-terminal amino acid sequence determined with the purified formate dehydrogenase was confirmed. In addition, the translation initiation site was accordingly determined and using the sequence down to the termination codon as an open reading frame, it was confirmed that this base sequence was homologous with the known formate dehydrogenase gene and that the protein encoded thereby corresponds to the molecular weight determined by electrophoresis. The base sequence of the thus-obtained DNA fragment containing the full length of the formate dehydrogenase gene is shown under SEQ ID NO:2 of the sequence listing, the base sequence of the open reading frame is shown under SEQ ID NO:3 of the sequence listing, and the amino acid sequence deduced from the base sequence is shown under SEQ ID NO:1 of the sequence listing.

EXAMPLE 6

Construction of a Recombinant Plasmid for High Expression of the Formate Dehydrogenase Gene Using the primers (Primer-7, Primer-8) having the sequences obtained by combining NdeI and PstI restriction sites to the N-terminal and C-terminal regions, respectively, of the formate dehydrogenase gene obtained in Example 4, the sequences of which are shown under SEQ ID NO:10 and NO:11, the DNA intermediate therebetween was amplified by PCR to acquire the open reading frame DNA fragment shown under SEQ ID NO:3 of the sequence listing.

Figure 2:
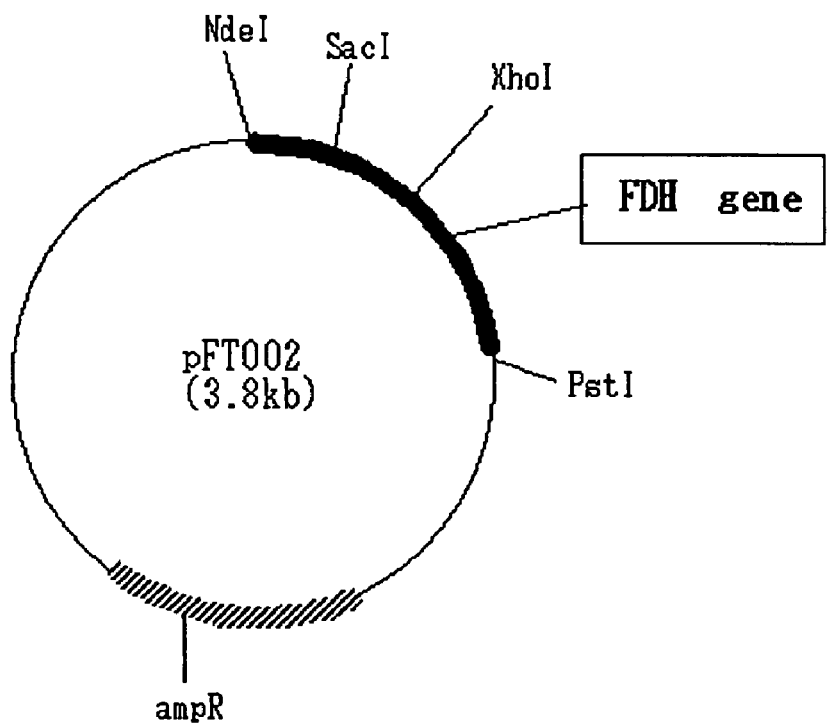
FIG. 2 is a restriction enzyme map of the recombinant plasmid pFT002 containing the formate dehydrogenase gene of the invention.

This DNA fragment was cleaved with restriction enzymes NdeI and PstI and, using a DNA ligase, combined to the vector plasmid pUCNT (WO 94/03613) cleaved with the same enzymes to construct a recombinant plasmid pFT002 designed so that the formate dehydrogenase gene might be expressed at a higher level as compared with pFT001 as represented by the restriction enzyme map in FIG. 2. In FIG. 2, "FDH gene" represents the formate dehydrogenase gene of the invention.

EXAMPLE 7

Construction of a Transformant Using a Recombinant DNA Containing the Formate Dehydrogenase Gene The recombinant plasmids pFT001 and pFT002 obtained in Example 5 and Example 6 were respectively admixed with competent cells of *Escherichia coli* HB101 for transformation and then plated on the agar medium shown in Table 4 to obtain the transformant *Escherichia coli* HB101 (pFT001) or *Escherichia coli* HB101 (pFT002) having the recombinant DNA containing the formate dehydrogenase gene as a colony.

TABLE 4

| | |
|---|---|
| Tryptone | 10 g |
| Yeast extract | 5 g |
| NaCl | 10 g |
| Agar | 15 g |
| Ampicillin | 100 mg |

The composition was made up to 1 L with deionized water, adjusted to pH 7, and sterilized by autoclaving. However, ampicillin was added after sterilization.

The transformant colony obtained was inoculated into 10 ml of the liquid medium shown in Table 5 and shake-cultured aerobically at 37° C. for 20 hours.

TABLE 5

| | |
|---|---|
| Tryptone | 16 g |
| Yeast extract | 10 g |
| NaCl | 5 g |
| Ampicillin | 100 mg |

The composition was made up to 1 L with deionized water, adjusted to pH 7, and sterilized by autoclaving. However, ampicillin was added after sterilization.

The cells were harvested by centrifuging the resulting culture medium, suspended in 0.1 M phosphate buffer (pH 7), disrupted by sonication, and centrifuged to remove cell-derived insolubles and give a transformant FDH enzyme solution. A 0.1 ml portion of this enzyme solution was mixed with 1.5 ml of 1 M sodium formate (pH 7 in 0.1 M phosphate buffer), 0.15 ml of 0.1 M NAD, and 1.25 ml of 0.1 M phosphate buffer (pH 7) and the change in absorbance at 340 nm was investigated at 30° C. As a result, increases in absorbance due to production of NADH were observed, indicating that both transformants had formate dehydrogenase activity.

EXAMPLE 8

Haloketone Tolerance of the Formate Dehydrogenase

The tolerance of this enzyme and other FDHs to various haloketones was investigated as follows. The recombinant *Escherichia coli* HB101 (pFT002) having the KNK65MA FDH gene-integrated pFT002 as obtained in Example 7 was inoculated into 100 ml of the liquid medium shown in Table 5 sterilizated in a 500 ml Sakaguchi flask, and shake-cultured aerobically at 37° C. for 20 hours. The resulting culture medium was centrifuged to harvest the cells, which were then suspended in 0.1 M phosphate buffer (pH 6.5), disrupted by sonication, and centrifuged to remove cell-derived insolubles and give a transformant FDH enzyme solution.

In the same manner, the recombinant *Escherichia coli* HB101 (pFA002) expressing the FDH derived from the KNK607 strain (WO 02/46427) was also cultivated to acquire a transformant FDH enzyme solution. Furthermore, *Candida boidinii* (ATCC 32195) was inoculated into 100 ml of the medium described in Example 1 (pH 6.0, however) and shake-cultured aerobically at 28° C. for 72 hours to similarly give an FDH enzyme solution.

To each of the three cell-free extracts thus prepared was added each of the various haloketones shown in Table 6 at 20 mM concentration (however, 2 mM for 1,1-dimethylethyl [(1S)-3-chloro-2-oxo-1-(phenylmethyl)propyl]carbamate and 10 mM for 1-(benzoyloxy)-3-chloro-2-propanone) in a ratio of 1:1 and after the mixture was allowed to stand at 30° C. for 5 hours (however, 28.5 hours in the case of 2-chloroacetophenone), the residual FDH activity was determined. The FDH activity was assayed by the method described in Example 7.

As shown in Table 6, the enzyme of the invention was confirmed to be highly tolerant to various haloketone compounds as compared with other FDHs. The residual FDH activity was expressed in the percent residual activity after treatment, with the activity of each untreated cell-free extract being taken as 100%.

TABLE 6

| Haloketone | | Residual FDH activity (%) | | |
|---|---|---|---|---|
| | | KNK65MA | KNK607 | *Candida boidinii* |
| 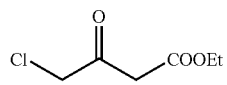 | Ethyl 4-chloroacetoacetate | 100.7 | 20.1 | 14.3 |
| 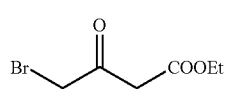 | Ethyl 4-bromoacetoacetate | 24.1 | 0.0 | 0.0 |
| 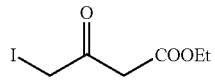 | Ethyl 4-iodoacetoacetate | 12.1 | 0.0 | 0.0 |

TABLE 6-continued
| Haloketone | | | Residual FDH activity (%) | | |
|---|---|---|---|---|---|
| | | | KNK65MA | KNK607 | Candida boidinii |
| 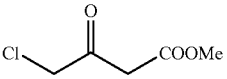 | | Methyl 4-chloroacetoacetate | 100.0 | 13.1 | 14.9 |
| 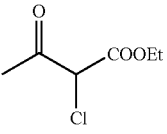 | | Ethyl 2-chloroacetoacetate | 100.0 | 2.5 | 5.4 |
| 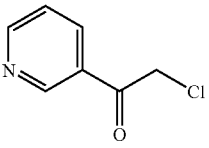 | | 2-Chloro-1-(3-pyridinyl)ethanone | 90.1 | 6.1 | 1.5 |
| 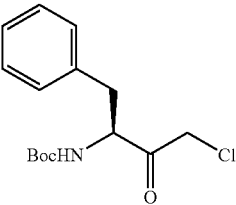 | | 1,1-Dimethylethyl [(1S)-3-chloro-2-oxo-1-(phenylmethyl)propyl] carbamate | 100.0 | 81.6 | 31.3 |
| 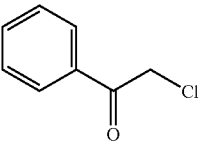 | | 2-Chloroacetophenone | 100.7 | 100.0 | 29.4 |
| 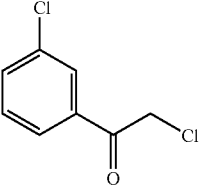 | | 2,3'-Dichloroacetophenone | 97.9 | 27.0 | 7.4 |
| 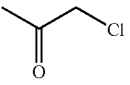 | | Chloroacetone | 100.0 | 46.2 | 38.2 |
| 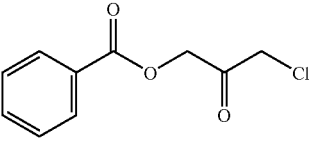 | | 1-(Benzoyloxy)-3-chloro-2-propanone | 100.7 | 1.6 | 4.5 |
| 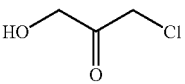 | | 1-Chloro-3-hydroxy-2-propanone | 80.1 | 11.7 | 14.7 |

EXAMPLE 9

Process for Regenerating a Coenzyme by Permitting an FDH Gene-Integrated Recombinant *Escherichia coli* to be Present in the Enzymatic Reduction System of Ethyl 4-Chloroacetoacetate

*Escherichia coli* HB101 (pFT002) expressing the KNK65MA-derived FDH as acquired in Example 7 and *Escherichia coli* HB101 (pFA002) expressing KNK607-derived FDH (WO 02/46427) were respectively inoculated into 60 ml of the liquid medium shown in Table 5 sterilized in a 500 ml Sakaguchi flask and shake-cultured at 37° C. for 9 hours. The resulting culture medium was inoculated into 100 ml of the liquid medium shown in Table 5 sterilized in a 500 ml Sakaguchi flask in size of 1% and shake-cultured at 37° C. for 46 hours. The resulting culture medium was centrifugally concentrated 5-fold and sonicated to give an FDH enzyme solution. On the other hand, for use as the reductase enzyme for reducing a 4-haloacetoacetate, the recombinant *Escherichia coli* HB101 (pNTS1M1)(FERM BP-8059) was inoculated into 100 ml of the medium shown in Table 5 sterilized in a 500 ml Sakaguchi flask, shake-cultured at 37° C. for 23 hours, and concentrated 10-fold and the cells were disrupted. To 6 ml of the above 5-fold concentrate of the FDH enzyme solution were added 9.25 ml of disrupted HB101 (pNTS1M1), 25 mg of NAD$^+$, 1 g of sodium formate, and 6 g of ethyl 4-chloroacetoacetate, followed by addition of 14.75 ml of ion-exchange water and 30 ml of butyl acetate to make a total of 60 ml. With the pH being controlled at 6.5 with 5 M aqueous formic acid solution, the reaction was carried out at 30° C. for 3.5 hours with stirring. After completion of the reaction, the reaction mixture was extracted with butyl acetate and the extract was analyzed. In the system where the coenzyme was regenerated by utilizing the FDH derived from KNK65MA according to the invention, ethyl 4-chloro-3-hydroxybutyrate was formed at a conversion rate of 100%. On the other hand, in the system utilizing the FDH derived from KNK607, ethyl 4-chloro-3-hydroxybutyrate was formed at a conversion rate of 26%.

The quantitation of ethyl 4-chloro-3-hydroxybutyrate was carried out by gas chromatography. Thus, using a glass column (ID 3 mm×1 m) packed with PEG-20M Chromosorb WAW DMCS 10%, 80/100 mesh (product of GL Sciences Inc.), chromatography was carried out at 150° C. The detection was made by FID.

INDUSTRIAL APPLICABILITY

The present invention provides a formate dehydrogenase having high specific activity, small Km values for formate and NAD, broad temperature and pH ranges of stability, broad temperature and pH ranges for action, and high tolerance to haloketones, thus being suited for industrial use. The invention further provides a DNA containing the gene coding for the above enzyme, a recombinant DNA constructed using a vector, and a transformant obtained by using this plasmid. The invention further provides an efficient process for producing said enzyme which is meritorious and has novel properties, and a process for regenerating a coenzyme with good efficiency which comprises permitting said enzyme to be present in the enzymatic reduction system of a haloketone or other compound.

---

The invention claimed is:

1. An isolated polynucleotide encoding a polypeptide of (a) or (b):
  (a) a polypeptide comprising the amino acid sequence of SEQ ID NO:1, or
  (b) a mutant of the polypeptide of (a), wherein said mutant polypeptide consists of one amino acid substitution, insertion, deletion or addition and said mutant polypeptide continues to have formate dehydrogenase activity.

2. An isolated polynucleotide of (a) or (b):
  (a) a polynucleotide comprising the nucleic acid sequence of SEQ ID NO:2 or
  (b) a mutant of the polynucleotide of (a), wherein said mutant polynucleotide consists of one nucleic acid substitution and said mutant polynucleotide encodes a polypeptide having formate dehydrogenase activity.

3. An isolated polynucleotide of (a) or (b):
  (a) a polynucleotide comprising the nucleic acid sequence of SEQ ID NO:3, or
  (b) a mutant of the polynucleotide of (a), wherein said mutant polynucleotide consists of one nucleic acid substitution and said mutant polynucleotide encodes a polypeptide having formate dehyd rogenase activity.

4. A recombinant plasmid comprising the polynucleotide according to claim 1.

5. The recombinant plasmid according to claim 4, wherein a pUC18, pUC19, pBR322, pACYC184, pSC101 or pUCNT vector is used.

6. The recombinant plasmid according to claim 4, which is comprised in *Escherichia coli* HB101 (pET001) (FERM BP-7672).

7. The recombinant plasmid according to claim 4, which is comprised in *Escherichia coli* HB101 (pFT002) (FERM BP-7673).

8. A microorganism transformed with the recombinant plasmid according to claim 4.

9. The transformed microorganism according to claim 8, wherein the microorganism is selected from microorganisms belonging to the following genera: *Escherichia, Pseudomonas, Flavobacterium, Bacillus, Serratia, Corynebacterium, Brevibacterium, Agrobacterium, Acetobacter, Giuconobacter, Lactobacillus, Streptococcus* and *Streptomyces*.

10. The transformed microorganism according to claim 8, wherein the microorganism is *Escherichia coil*.

11. The transformed microorganism according to claim 8, wherein the microorganism is *Escherichia coil* HB101.

12. The transformed microorganism according to claim 8, which is *Escherichia coil* HB101 (pFT001) (FERM BP-7672) or *Escherichia coil* HB101 (pFT002) (FERM BP-7673).

13. A process for producing a polypeptide having formate dehydrogenase activity,
  which comprises cultivating a strain of microorganism that produces the polypeptide and accumulates said polypeptide in the resulting culture medium and harvesting the same,
  wherein the polypeptide is the polypeptide of (a) or (b):
  (a) a polypeptide comprising the amino acid sequence of SEQ ID NO:1 or
  (b) a mutant of the polypeptide of (a), wherein said mutant polypeptide consists of one amino acid substitution, insertion, deletion or addition and said mutant polypeptide continues to have formate dehydrogenase activity.

14. The process according to claim 13,
  wherein the strain of microorganism belongs to the genus *Thiobacillus*.

15. The process according to claim 14,
  wherein the strain of microorganism belongs to the genus *Thiobacillus* sp. KNK65MA (FERM BP-7671).

16. A process for producing a formate dehydrogenase,
  which comprises cultivating the transformed microorganism according to claim 8 to express and accumulate the formate dehydrogenase in the resulting culture medium and harvesting the same.

* * * * *